United States Patent [19]
Babler

[11] Patent Number: 5,872,277
[45] Date of Patent: Feb. 16, 1999

[54] METHODS FOR PREPARING PRENYL ALCOHOL

[75] Inventor: James H. Babler, Chicago, Ill.

[73] Assignee: Loyola University of Chicago, Chicago, Ill.

[21] Appl. No.: 814,472

[22] Filed: Mar. 10, 1997

[51] Int. Cl.$^6$ ..................................................... C07C 67/02
[52] U.S. Cl. ........................... 560/261; 560/129; 568/877
[58] Field of Search .................................... 560/261, 129; 568/877

[56] References Cited

FOREIGN PATENT DOCUMENTS

| 30 21 414 A | 11/1980 | Germany . |
| 3105399 | 10/1982 | Germany . |
| 2 238 539 A | 5/1991 | United Kingdom . |

OTHER PUBLICATIONS

Chem. Abstracts 1981, 95, 7513q OF European patent application 21, 074 (Jan. 7, 1981, filed by BASF).
Chem. Abstracts 1990, 112, 179516d OF European patent application EP 344,043 (Nov. 29, 1989) filed by Rhône-Poulenc.
Chem. Abstracts 1975, 82, 4434k OF German patent 2,411, 530 (Sep. 26, 1974 to Hoffmann–LaRoche).
Chem. Abstracts 1978, 88, 89114c OF German patent 2,625, 074 (Dec. 8, 1977 to BASF).
Chem. Abstracts 1979, 91, 123406y. OF German patent 2,423,409 (Nov. 28, 1974 to Teijin Ltd. of Japan).
Chem. Abstracts 1981, 94, 174311h OF German patent 3,021,414 Dec. 11, 1980, issued to Montedison.
Chem. Abstracts 1972, 77, 153520j OF Japanese patent 71 14,107, issued to Sumitomo Chemical Co., Ltd.
Chem. Abstracts 1977, 87, 38852p OF Japanese patent 77 10,207 issued to Kuraray Co., Ltd.
Chem. Abstracts 1986, 104, 148312q OF Japanese patent 60 239,443 issued to Kuraray Co., Ltd.
Chem. Abstracts 1986, 105, 134188n OF Japanese patent 61 22,038 issued to Kuraray Co., Ltd.
Chem. Abstracts 1991, 115, 114815t OF PCT Int. Appl. WO 91 09,830 (Jul. 11, 1991).
Chem. Abstracts 1977, 87, 136042u OF U.S. patent 4,016, 212 (Apr. 5, 1977 to Hoffmann–LaRoche).
Boyd, R., Morrison, R., "Effect of substituents on acidity" Organic Chemistry, Sixth Edition, p. 735.
Babin, D., Fourneron, J., Julia, M., "Condensations biomimétiques: édification de squelettes terpéniques à partir de synthons isopréniques" Bull. Soc. Chim. France, 1980, Part II, 588.
Matsumoto, M., Watanabe, N., "Oxidation of Allylic Alcohols to Unsaturated Carbonyl Compounds by Ruthenium Dioxide and Dioxygen/Ruthenium Dixoxide" J. Org Chem. 1984, 49, 3435.
Cope, A. Ed, "β–Carbethoxy–y,y–Diphenylvinylacetic Acid" Org. Synth. 30, 18(1950).
Skolnik, H., "Hydration of isoprene with a cation–exchange resin catalyst" Chem. Abstracts 1973, 78, 84547e.
T. Lennartz: "Synthesen von aliphatischen Terpenalkoholen aus Isopren" Berichte Der Deutschen Chemischen Gesellschaft, vol. 43, No. 8, 1943, Weinheim DE, pp. 831–846, XP002064850 see p. 841.
M.A. Rachita, et al.: "Ruthenium(II) catalyzed ring closure of prochiral .alfpha.–chloro–N–tosyl amides: a diastereoselectivity study" Tetrahedron Letters, vol. 34, No. 43, 22 Oct. 1993, Oxford, GB, pp. 6821–6824, XP002064851 see p. 6821, paragraph 2.

*Primary Examiner*—Paul J. Killos
*Attorney, Agent, or Firm*—Marshall, O'Toole, Gerstein, Murray & Borun

[57] ABSTRACT

Methods for preparing 3-methyl-2-buten-1-ol (prenyl alcohol) from 2-methyl-1,3-butadiene (isoprene) and carboxylic acids are disclosed. Carboxylic acids which can be used in the process have a $K_a$ (relative to water) greater than $10^{-4}$; dichloroacetic acid is especially preferred. The process involves the slow (e.g., dropwise) addition of isoprene to the carboxylic acid to form a prenyl ester. The ester-formation reaction proceeds at room temperature in most cases; use of an organic base catalyst, preferably a sodium or potassium salt of the reactant carboxylic acid, improves the yield. The resultant prenyl ester can be converted to prenyl alcohol by reaction with a base. Prenyl alcohol can be readily converted to citral, a chemical intermediate in the synthesis of vitamins A and E, and several widely-used carotenoids.

18 Claims, No Drawings

METHODS FOR PREPARING PRENYL ALCOHOL

BACKGROUND OF THE INVENTION

1. Field of the Invention

The present invention relates to methods for preparing prenyl alcohol (3-methyl-2-buten-1-ol) and ester derivatives of prenyl alcohol. Prenyl alcohol is an intermediate in the manufacture of citral, a specialty chemical used in the flavor and fragrance industries, as well as in the manufacture of vitamins A and E, the anti-acne drugs Retin-A and Accutane®, and several widely-used carotenoids, including beta-carotene.

One of the most expedient routes to citral (5) involves a thermal rearrangement of 3-methyl-1-(3-methyl-2-buten-1-oxy)-1,3-butadiene (4), which is readily obtained when acetal 3 [prepared from prenyl alcohol, 2 and 3-methyl-2-butenal (prenal, 1)] is heated in the presence of a weak acid catalyst (e.g., acetic acid or 2,4-dinitrophenol) at temperatures in the range of 125°–150° C. The pathway by which unsaturated ether 4 is converted to citral (5) involves a Claisen rearrangement, followed by a subsequent Cope rearrangement in the same reaction vessel:

$(CH_3)_2C=CHCH=O$ +

1

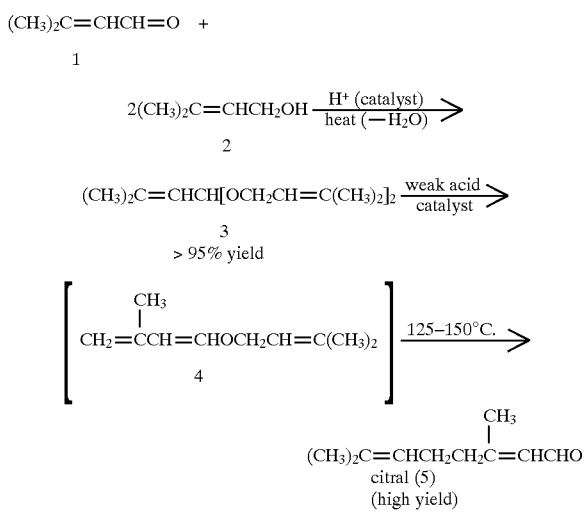

The approach to citral described above has been known for more than 25 years and has continued to be developed to the stage where one is able to effect the conversion of prenal (1) and prenyl alcohol (2) to citral (5) in a "one-pot" process. See, European patent application EP 344,043 (Nov. 29, 1989) filed by Rhône-Poulenc [*Chem. Abstracts* 1990, 112, 179516d] and PCT Int. Appl. WO 91 09,830 (Jul. 11, 1991) [*Chem. Abstracts* 1991, 115, 114815t]. Previous patents have verified that unsaturated ether 4 (obtained directly from acetal 3) can be converted to citral in high yield (90–100%), e.g.:

(a) German patent 2,411,530 (Sep. 26, 1974 to Hoffmann-LaRoche): *Chem. Abstracts* 1975, 82, 4434k.
(b) U.S. Pat. No. 4,016,212 (Apr. 5, 1977 to Hoffmann-LaRoche): *Chem. Abstracts* 1977, 87, 136042u.
(c) German patent 2,423,409 (Nov. 28, 1974 to Teijin Ltd. of Japan): *Chem. Abstracts* 1979, 91, 123406y.
(d) German patent 2,625,074 (Dec. 8, 1977 to BASF): *Chem. Abstracts* 1978, 88, 89114c.
(e) European patent application 21,074 (Jan. 7, 1981, filed by BASF): *Chem. Abstracts* 1981, 95, 7513q.
(f) Japanese patent 61 22,038 issued to Kuraray Co., Ltd.: *Chem. Abstracts* 1986, 105, 134188n.

The principal difficulty with the above process is the high cost of prenyl alcohol—which is almost as costly as citral. Once prenyl alcohol (2) is obtained, however, it can be conveniently oxidized with air in the presence of various metallic or metallic salt catalysts to yield the corresponding aldehyde [prenal (1)]. Refer to: M. Matsumoto, et al.,*J. Org. Chem.* 1984, 49, 3435, and Japanese patent 60 239,443 issued to Kuraray Co., Ltd. [*Chem. Abstracts* 1986, 104, 148312q].

2. Description of Related Art

Isoprene [2-methyl-1,3-butadiene, $CH_2=C(CH_3)CH=CH_2$] would seem to be a useful and potentially low-cost precursor to prenyl alcohol (2). Isoprene, which is used to make "synthetic natural rubber," can be obtained by "cracking" petroleum or—more conveniently—by a Prins reaction involving isobutylene and formaldehyde:

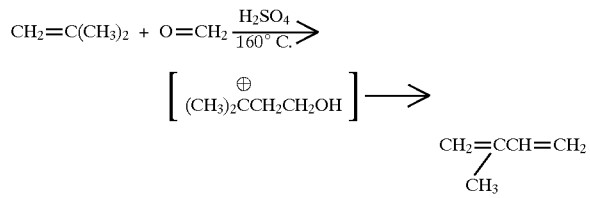

See, Japanese patent 71 14,107, issued to Sumitomo Chemical Co., Ltd. [*Chem. Abstracts* 1972, 77, 153520j].

Unfortunately, acid-catalyzed addition of water to isoprene yields only a minor amount of prenyl alcohol and a substantial amount of the isomeric tertiary alcohol shown below:

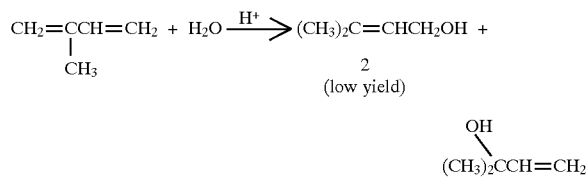

In addition to the above two alcohols, various other products are obtained in this reaction. Reference: *Chem. Abstracts* 1973, 78, 84547e.

Another approach to the formation of prenyl alcohol (2) from isoprene involves the addition of hydrohalic acids (HX: HCl or HBr) to isoprene. Although this reaction does yield prenyl halides [$(CH_3)_2C=CHCH_2X$, X=Br or Cl], yields are only moderate and the reaction is complicated by the fact that HX also adds to the double bond in the initially formed prenyl halide to give a dihalide:

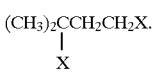

Furthermore, prenyl bromide (or chloride) is highly toxic, rather volatile, and decomposes if one attempts to distill it at atmospheric pressure. On the other hand, if one has prenyl halides (6) available, the following route to prenyl alcohol has been developed:

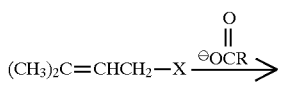

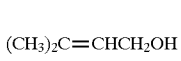

Refer to: Japanese patent 77 10,207 issued to Kuraray Co., Ltd. [*Chem. Abstracts* 1977, 87, 38852p] and German patent 3,021,414 (Dec. 11, 1980, issued to Montedison; *Chem. Abstracts* 1981, 94, 174311h).

SUMMARY OF THE INVENTION

1. Synthesis of Prenyl Esters

A facile method for converting isoprene in high yield to certain prenyl esters (7) has been developed. The process is easy to conduct and involves dropwise addition of isoprene (bp: 34° C.) to a carboxylic acid (8) whose $K_a$ (relative to water) is greater than $10^{-4}$ to afford the corresponding ester (7):

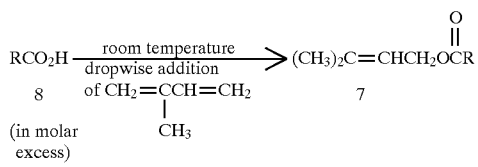

Because the prenyl esters will be subsequently hydrolyzed, mixtures of carboxylic acids, $RCO_2H$, can also be employed. This reaction will not occur unless the carboxylic acid (8) has a $K_a$ (relative to water) greater than $10^{-4}$ (i.e., a $pK_a$ less than 4). The reaction fails for acetic acid ($K_a$ $1.75 \times 10^{-5}$), propionic acid ($K_a = 1.34 \times 10^{-5}$), et al., and is even quite slow when one uses formic acid ($K_a = 1.77 \times 10^{-4}$; see, Example VI). (A list of $K_a$s for various carboxylic acids is reported at page 735 of *ORGANIC CHEMISTRY*, Sixth Edition, by Morrison and Boyd, the disclosure of which is incorporated herein). Thus, R is H or an organic group, preferably $C_1$ to $C_4$ haloalkyl, which when part of a carboxylic acid (8) has a $K_a$ (relative to water) greater than $10^{-4}$.

If one adds a very strong acid ($K_a$ greater than $10^2$), such as sulfuric acid or p-toluenesulfonic acid, to a representative carboxylic acid such as acetic acid, the desired reaction will occur; but yields of prenyl esters are low (less than 25%), perhaps because the ester product (7) itself is sensitive to strongly acidic conditions.

In contrast, the use of dichloroacetic acid (a liquid, bp: 194° C.; $K_a = 5.53 \times 10^{-2}$) in molar excess in the above reaction results in a moderate yield (approximately 50%) of the corresponding ester (prenyl dichloroacetate, systematically named, 3-methyl-2-buten-1-yl dichloroaceate). Addition of a minor amount of an alkali-metal or alkaline-earth metallic salt or metallic salt of dichloroacetic acid (i.e., the conjugate base of dichloroacetic acid) to the reaction mixture containing dichloroacetic acid resulted in a better conversion of isoprene to prenyl dichloroacetate: 70–95% yields of the ester were obtained. This metallic salt is continuously regenerated in the reaction process.

Since dichloroacetic acid is a liquid, no additional solvent is needed, although adding acids such as acetic acid or formic acid as cosolvents is a feasible modification of this invention. Once the ester (7) is obtained, it can be readily saponified using sodium carbonate, sodium hydroxide, potassium carbonate, et al. in aqueous alcohol at room temperature. No tertiary alcohol esters (9) isomeric with 7, were observed in the products formed in the process of the present invention:

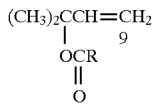

In contrast, when water is added to isoprene, a major product is the tertiary alcohol, $(CH_3)_2C(OH)CH=CH_2$. Reference: *Chem. Abstracts* 1973, 78, 84547e.

The process of the present invention involves protonation of isoprene to yield the prenyl cation: $(CH_3)_2C=CHCH_2^{\oplus}$. This cation is known to react with unsaturated esters, [such as $$CH_2=C(CH_3)CH_2CH_2OCCH_3]$$
$$\qquad\qquad\qquad\qquad\quad \|$$
$$\qquad\qquad\qquad\qquad\quad O$$

similar to the structure of ester 7. See, Table X, entries 5 and 7 on page 595 in an article by Julia and coworkers: *Bull. Soc. Chim.* France, 1980, Part II, 588. Entry 5 refers to the following reaction:

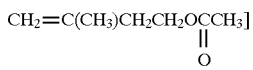

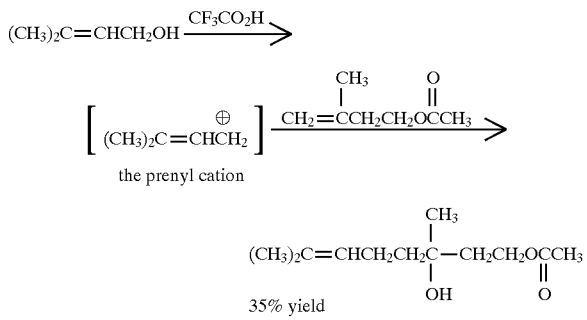

Entry 7 of the Julia reference is similar; however, it uses formic acid in molar excess and a prenyl ester (i.e., prenyl formate) to generate the prenyl cation.

Thus, the literature teaches that the prenyl cation (generated in the presence of carboxylic acids) adds readily to the alkene functionality in unsaturated esters to give higher molecular weight adducts—terpenes in the examples cited above. Since the process of the present invention involves both the prenyl cation (generated by protonation of isoprene) and unsaturated esters [i.e., formation of prenyl esters (7)], the obtention of the latter (7) in high yield was surprising: based on the prior art, one would expect subsequent reaction of the initially-formed prenyl ester (7), in the presence of a carboxylic acid, to re-generate the prenyl cation—eventually leading to dimeric products.

2. Synthesis of Starting Materials

The preferred reactants employed in the method of the present invention—isoprene and dichloroacetic acid—are commercially available. If one so desires, these reactants can be synthesized. For example, isoprene can be formed by reacting isobutylene (2-methylpropene) with formaldehyde at about 160° C. using a sulfuric acid catalyst. Dichloroacetic acid can be formed in several ways:

a) By reacting chloroacetic acid with chlorine using a PCl$_3$ catalyst;
b) By reacting acetaldehyde with excess chlorine to form trichloroacetaldehyde—Cl$_3$CCHO. When dissolved in an aqueous mixture of calcium carbonate and sodium cyanide, and heated to about 85° C., trichloroacetaldehyde can be converted to dichloroacetic acid; or
c) Trichloroacetic acid can be electrolytically reduced to dichloroacetic acid.

3. Process Steps For Procedure

The following are important elements in the processes of the present invention:

(a) An alkanoic acid, pk$_a$ (relative to water) <4, in molar excess. Mixtures of such acids; or a concentrated solution (greater than 1 M) of such an acid in a weaker acid solvent (e.g., acetic or propionic acid) can also be used. However, for the stronger/weaker acid type of solvent system, the process is quite slow.

(b) Slow addition of isoprene (e.g., dropwise addition over a period of several hours) to the alkanoic acid is required for a good yield. If isoprene is added in one portion, the prenyl cation [(CH$_3$)$_2$C=CHCH$_2$$^\oplus$] generated by protonation of isoprene can react with another isoprene to give polymeric terpenes, rather than being trapped by RCO$_2$H or RCO$_2$$^\ominus$ to yield the desired prenyl ester (7).

(c) The reaction occurs readily at room temperature; thus heating is not required. However, absent heating, the reaction proceeds very slowly when formic acid is employed (Example VI).

(d) The presence of an organic base, (R'CO$_2$)$_x$M, where M is a Group I or Group II cation and x is 1 or 2, is not necessary, but is desirable for optimizing yields of prenyl esters (7). R'CO$_2$$^\ominus$ is better at trapping the prenyl cation than is the carboxylic acid itself. The conjugate base (RCO$_2$$^-$) of the reactant carboxylic acid is preferred. However, other carboxylate bases can also be used. For example, the strongest base one can have in appreciable quantity in dichloroacetic acid is Cl$_2$CHCO$_2$$^\ominus$. If one adds sodium acetate (a stronger base) to dichloroacetic acid, a reaction occurs to yield acetic acid (a weaker acid) and sodium dichloroacetate (a weaker base). Thus, the process can be conducted by using the "strong" carboxylic acid in excess (e.g., Cl$_2$CHCO$_2$H) and adding a salt of a weaker carboxylic acid (e.g., sodium propionate or potassium acetate) to generate the desired carboxylate anion (Cl$_2$CHCO$_2$$^-$) in situ.

4. Formation of Citral From Isoprene and Dichloroacetic Acid

A preferred reaction using dichloroacetic acid and sodium dichloroacetate is as follows:

Step A:

Cl$_2$CHCO$_2$H +
molar excess
(100% re-cyclable, since it is water-miscible and virtually insolbule in heptane, octane, et al.)

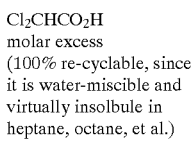
NaOCCHCl$_2$ (10)
(Can be prepared in situ by addition of sodium acetate to dichloroacetic acid)

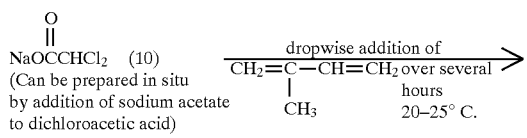
dropwise addition of
CH$_2$=C—CH=CH$_2$ over several
       |          hours
       CH$_3$     20–25° C.

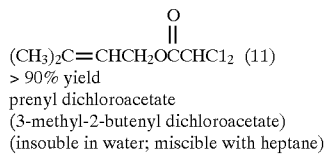
(CH$_3$)$_2$C=CHCH$_2$OCCHCl$_2$ (11)
> 90% yield
prenyl dichloroacetate
(3-methyl-2-butenyl dichloroacetate)
(insouble in water; miscible with heptane)

NOTE: Sodium dichloroacetate (10) is not consumed in this reaction.

Product isolation is rather easy: either continuously extract the prenyl dichloroacetate product (11) from the mixture using heptane, octane, or a similar non-polar organic solvent, or partition the mixture between the non-polar solvent and water. All dichloroacetic acid remains in the aqueous phase. Removal of the water by distillation at 20–25 mm (reference: *J. Am. Chem. Soc.* 1931, 53, 1594) allows for total recovery of Cl$_2$CHCO$_2$H and sodium dichloroacetate.

Step B:

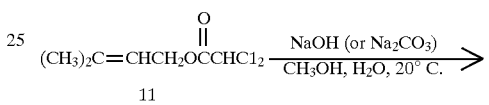
(CH$_3$)$_2$C=CHCH$_2$OCCHCl$_2$ $\xrightarrow[\text{CH}_3\text{OH, H}_2\text{O, 20° C.}]{\text{NaOH (or Na}_2\text{CO}_3\text{)}}$
11

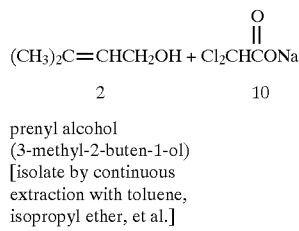
(CH$_3$)$_2$C=CHCH$_2$OH + Cl$_2$CHCONa
2                                    10
prenyl alcohol
(3-methyl-2-buten-1-ol)
[isolate by continuous extraction with toluene, isopropyl ether, et al.]

After isolation of prenyl alcohol, the aqueous phase can be acidified with dilute H$_2$SO$_4$ and Cl$_2$CHCO$_2$H can be recovered by continuous extraction with isopropyl acetate, et al.

Step C:
(CH$_3$)$_2$C=CHCH$_2$OH $\xrightarrow[300° \text{C.}]{\text{O}_2\text{, Cu(NO}_3\text{)}_2 \text{ (catalyst)}}$
2

(CH$_3$)$_2$C=CHCH=O
1

References: *Chem Abstracts* 1986, 104, 148312q. Also see: *J. Org Chem.* 1984, 49, 3435.

Last step in the manufacture of Citral:

Either:

(a) (CH$_3$)$_2$C=CHCHO +
    1

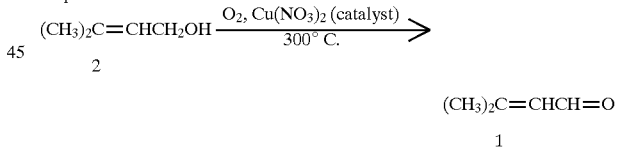
2 (CH$_3$)$_2$C=CHCH$_2$OH $\xrightarrow[80° \text{C., 60mm}]{\text{(NH}_4\text{)}_2\text{SO}_4 \text{ or} \atop \text{MgSo}_4 \text{(catalyst)}}$
2

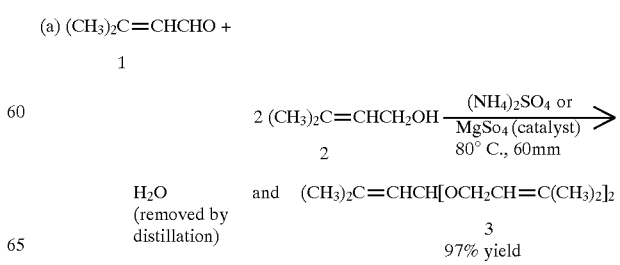
H$_2$O         and  (CH$_3$)$_2$C=CHCH[OCH$_2$CH=C(CH$_3$)$_2$]$_2$
(removed by                            3
distillation)                    97% yield Reference: *Chem Abstracts* 1986, 105, 134188n

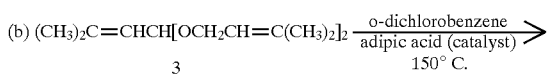

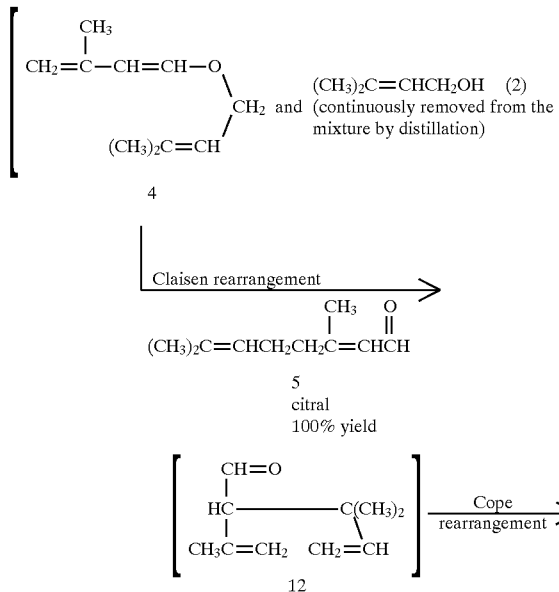

Or:

a "one-pot" process:

$(CH_3)_2C=CHCH=O$ +

1
prenal $2(CH_3)_2C=CHCH_2OH \xrightarrow[\text{toluene}]{H_3PO_4 \text{ (catalyst)}}$ 2
prenyl alcohol $(CH_3)_2C=CHCH[OCH_2CH=C(CH_3)_2]_2$

3

$\xrightarrow[\text{neutralize } H_3PO_4 \text{ and continue}]{\text{add potassium acetate to}}$
heating at 125–140° C. (90mm)

$(CH_3)_2C=CHCH_2CH_2\overset{CH_3}{\underset{|}{C}}=\overset{O}{\underset{\|}{C}}HCH$ 5
citral
(3, 7-dimethyl-2, 6-octadienal)

Reference: *Chem. Abstracts* 1991, 115, 114815t.

DETAILED DESCRIPTION OF THE INVENTION

The following examples are presented for purposes of illustration and should not be construed as limiting the invention which is delineated in the claims.

EXAMPLE I

Preparation of 3-Methyl-2-buten-1-yl Dichloroacetate by Treatment of Isoprene With Dichloroacetic Acid Containing Sodium Dichloroacetate 154 mg (1.02 mmoles) of sodium dichloroacetate (purchased from Aldrich Chemical Co., Milwaukee, Wis.) and 4.00 ml (48.5 mmoles) of dichloroacetic acid (purified-grade, purchased from Fisher Scientific Co.) were added to a 25 ml, 3-neck reaction flask fitted with a septum cap (to allow addition of isoprene to be made using a 10 μL syringe) and an adapter connected to an apparatus similar to that described by Johnson and Schneider [*Org. Synth.* 30, 18(1950)] so that the mixture in the flask could be protected from atmospheric moisture throughout the course of the reaction. This mixture was stirred for several minutes at room temperature until all solid had dissolved, after which the reaction was initiated by addition of 5.0 microliters (μL) of isoprene (purchased from Aldrich Chemical Co., Milwaukee, Wis.) to the stirred reaction mixture. Every two minutes, an additional portion (5.0 μL) of isoprene was added until 50 such portions (50×5 μL; 2.50 mmoles) of isoprene had been added over a period of 98 minutes. The mixture was subsequently stirred at room temperature for an additional 10 minutes. The product was isolated by dilution of the reaction mixture with 35 ml of 10% (w/v) aqueous sodium chloride (NOTE: only water should be used, if one intends to recycle dichloroacetic acid and sodium dichloroacetate.) and extraction with 25 ml of hexane. After subsequent washing of the organic layer with saturated aqueous sodium bicarbonate (1×25 ml) and saturated aqueous sodium chloride (1×25 ml), it was dried over anhydrous magnesium sulfate and filtered. Removal of the hexane by evaporation at reduced pressure and subsequent evaporative distillation afforded 348 mg (71% yield) of the named prenyl ester: boiling point 78°–92° C. (bath temperature, 0.30 mm). The identity and purity of this compound was ascertained by IR and proton NMR analysis (recorded at 400 MHz). The latter spectrum exhibited a singlet at δ5.94(CHCl$_2$), a triplet of quartets (J=7.2, 1.4 Hz) at δ5.385 (CH=C), a doublet (J=7.2 Hz) at δ4.76 (CH$_2$ O), and signals for two vinyl methyl groups at δ1.748 and 1.737.

If one desires to maximize the yield of prenyl dichloroacetate, the presence of additional sodium dichloroacetate and/or the controlled addition of isoprene, using a syringe pump, over a period of several hours are recommended.

EXAMPLE II

Preparation of 3-Methyl-2-buten-1-ol (Prenyl Alcohol) by Saponification of Prenyl Dichloroacetate To a solution of 3-methyl-2-buten-1-yl dichloroacetate (536 mg, 2.72 mmoles), produced from isoprene on a larger scale in accordance with Example I, in 3.0 ml of methyl alcohol was added 0.75 ml of 5M aqueous sodium hydroxide (3.75 mmoles). This mixture was subsequently stirred at room temperature for 90 minutes. The product was isolated by dilution of the reaction mixture with 30 ml of saturated aqueous sodium chloride and extraction with 20 ml of 1:1 (v/v) pentane:ether. [NOTE: if one desires to recycle sodium dichloroacetate, continuous extraction of prenyl alcohol from the reaction mixture by use of a suitable organic solvent (e.g., isopropyl acetate) is recommended]. After subsequent washing of the organic layer with saturated aqueous sodium chloride (25 ml), it was dried over anhydrous magnesium sulfate and filtered. Removal of most of the volatile organic solvents by fractional distillation at atmospheric pressure, followed by removal of residual pentane at reduced pressure (60 mm), afforded 207 mg (88% yield) of the named alcohol, the IR and proton NMR spectral properties of which were identical to those exhibited by an authentic sample of 3-methyl-2-buten-1-ol (purchased from Aldrich Chemical Co., Milwaukee, Wis.).

EXAMPLE III

Preparation of 3-Methyl-2-buten-1-yl Dichloroacetate by Treatment of Isoprene With Dichloroacetic Acid Containing Potassium Dichloroacetate 162 mg (0.97 mmole) of potassium dichloroacetate (purchased from Aldrich Chemical Company, Milwaukee, Wis.) [NOTE: one can also prepare the latter salt in situ by addition of potassium acetate to dichloroacetic acid.] and 4.00 ml (48.5 mmoles) of dichloroacetic acid (purified-grade, purchased from Fisher Scientific Co.) were added to a reaction flask identical to that described in the procedure of Example I. Once all solid had dissolved, the reaction was initiated by addition of 10 μL of isoprene (purchased from Aldrich Chemical Co., Milwaukee, Wis.) to the stirred reaction mixture at room temperature. Every minute, an additional portion (10 μL) of isoprene was added until 30 such portions (30×10 μL; 3.00 mmoles) of isoprene had been added over a period of 29 minutes. The mixture was subsequently stirred at room temperature for an additional 10 minutes. Isolation of product as described in the procedure of Example I, followed by evaporative distillation, afforded 301 mg (51% yield) of the named ester, the boiling point and spectral properties of which were identical to those exhibited by the product prepared in accordance with the procedure of Example I.

To verify that the lower yield of prenyl dichloroacetate obtained using the above procedure (vs. that obtained in Example I) was due to a more rapid addition of isoprene to the reaction mixture (allowing the prenyl cation to react with isoprene instead of dichloroacetate, thereby yielding more "dimeric, higher-boiling" products), this procedure (using identical quantities of potassium dichloroacetate and dichloroacetic acid) was repeated with the following modification: add 10 μL portions of isoprene to the reaction mixture every two minutes until 30 such portions (30×10 μL; 3.00 mmoles) of isoprene had been added over a period of 58 minutes. As expected, this modification resulted in a significant increase in the distilled yield (372 mg, 63%) of prenyl dichloroacetate. The fact that a higher yield (63% vs. 51%) of the latter ester was obtained by lengthening the time over which isoprene is added to the reaction mixture indicates that the product, once formed, is reasonably stable under these reaction conditions.

EXAMPLE IV

Preparation of Prenyl Esters by Treatment of Isoprene With a Mixture of Carboxylic Acids Containing a Carboxylate Salt 102 mg (1.24 mmoles) of anhydrous sodium acetate and 1.048 g (6.41 mmoles) of trichloroacetic acid (purchased from Aldrich Chemical Co., Milwaukee, Wis.) were added to 3.00 ml (36.4 mmoles) of dichloroacetic acid (purified-grade, purchased from Fisher Scientific Co.) in a reaction flask identical to that described in the procedure of Example I. Once all solid had dissolved, the reaction was initiated by addition of 10 μL of isoprene to the stirred reaction mixture at room temperature. Every minute, an additional portion (10 μL) of isoprene was added until 30 such portions (30×μL; 3.00 mmoles) of isoprene had been added over a period of 29 minutes. The mixture was subsequently stirred at room temperature for an additional 10 minutes. Isolation of the product as described in the procedure of Example I afforded 530 mg (89.7% yield, if isoprene had been converted solely to prenyl dichloroacetate) of a mixture, shown by proton NMR analysis to contain prenyl dichloroacetate and prenyl trichloroacetate in a 2.5:1 ratio. Prenyl trichloroacetate (3-methyl-2-buten-1-yl trichloroacetate) was characterized by a doublet (J=7 Hz) at δ4.85 ($CH_2O$), whereas the corresponding signal for prenyl dichloroacetate was a doublet centered at δ4.76. Proton NMR analysis also indicated that approximately 20–25% of the crude product was a mixture of unidentified, dimeric high-boiling compounds—similar to the by-products observed in the procedure described in the first part of Example III. Prenyl dichloroacetate can be readily separated from these by-products by distillation (as shown in Examples I and III).

EXAMPLE V

Attempt to Prepare 3-Methyl-2-buten-1-yl Propionate by Treatment of Isoprene With Propionic Acid 119 mg (1.24 mmoles) of sodium propionate (purified-grade, purchased from Fisher Scientific Co.), 0.25 ml (2.50 mmoles) of isoprene, and 5.00 ml of propionic acid (99+% purity, purchased from Aldrich Chemical Co., Milwaukee, Wis.) were added to a reaction flask equipped with an efficient reflux condenser connected to an apparatus similar to that described by Johnson and Schneider [*Org. Synth.* 30, 18 (1950)] so that the mixture in the flask could be protected from atmospheric moisture throughout the course of the reaction. This mixture was subsequently stirred at room temperature for 3 hours. Isolation of the product as described in the procedure of Example I afforded 11 mg of material, the infrared spectrum of which exhibited no carbonyl absorption peak. Hence, isoprene cannot be converted into a prenyl ester using such weakly acidic conditions.

EXAMPLE VI

Preparation of 3-Methyl-2-buten-1-yl Formate by Addition of Formic Acid to Isoprene 143 mg (2.10 mmoles) of sodium formate, 0.25 ml (2.50 mmoles) of isoprene, and 6.00 ml of 98–100% formic acid were added to a reaction flask equipped with an efficient reflux condenser connected to an apparatus similar to that described by Johnson and Schneider [*Org. Synth.* 30, 18 (1950)] so that the mixture in the flask could be protected from atmospheric moisture throughout the course of the reaction. This mixture was subsequently stirred at room temperature for 4 hours. The product was isolated by dilution of the reaction mixture with 50 ml of 10% (w/v) aqueous sodium chloride and extraction with 30 ml of pentane. After subsequent washing of the organic layer with saturated aqueous sodium bicarbonate (1×25 ml) and saturated aqueous sodium chloride (1×25 ml), it was dried over anhydrous magnesium sulfate and filtered. In order to minimize loss of volatile prenyl formate, the dried organic layer was then concentrated to a volume of 3–4 ml by removal of most of the pentane via fractional distillation at atmospheric pressure. Residual pentane was then removed by evaporation at reduced pressure to yield 38 mg (13% yield, based on conversion of isoprene to prenyl formate) of crude product. Subsequent proton NMR analysis indicated that prenyl formate comprised slightly less than half of this crude mixture, and hence the conversion of isoprene to the desired ester was only approximately 5%.

To demonstrate that the reaction was more facile when conducted in a more acidic carboxylic acid (i.e., $K_a$ greater than $10^{31\ 3}$), a similar experiment was run using 161 mg (0.96 mmole) of potassium dichloroacetate (purchased from Aldrich Chemical Co., Milwaukee, Wis.), 5.00 ml of dichloroacetic acid (purified-grade, purchased from Fisher Scientific Co.), and 0.25 ml (2.50 mmoles) of isoprene. This mixture was stirred at room temperature for only 30 minutes, after which the product was isolated in the manner described above, affording 287 mg (58% yield—if the product were solely prenyl dichloroacetate) of a mixture, approximately half of which was the desired prenyl ester. Although the reaction occurred rapidly in dichloroacetic acid, the yield of prenyl dichloroacetate was significantly diminished (25–30% yield at best) by the failure to add isoprene slowly to the acidic reaction mixture.

NOTE: If one wants to obtain prenyl formate in higher yield by this process, it will be necessary to add isoprene slowly to a heated mixture (e.g., 40°–100° C.) of formic acid containing a formate salt in a pressure vessel (due to isoprene's boiling point of 34° C.).

EXAMPLE VII

Preparation of 3-Methyl-2-buten-1-yl Dichloroacetate by Treatment of Isoprene With Dichloroacetic Acid in the Absence of Dichloroacetate Salts Using the procedure described in Example VI, a solution of 0.25 ml (2.50 mmoles) of isoprene in 5.00 ml of dichloroacetic acid (purified-grade, purchased from Fisher Scientific Co.) was stirred at room temperature for 30 minutes. Isolation of the product as described in the procedure of Example VI afforded 216 mg (44%, not corrected for impurities) of a mixture containing the named ester (less than 50% of the mixture) and by-products derived from "dimerization/polymerization" of isoprene (i.e., the prenyl cation reacting with isoprene rather than being trapped by dichloroacetate). Although the reaction proceeds in dichloroacetic acid, a comparison of this product mixture with that obtained in the second part of Example VI (i.e., a similar experiment, but conducted in the presence of a dichloroacetate salt) demonstrates the beneficial effect that the latter salt has on the yield of the desired prenyl ester.

EXAMPLE VIII

Preparation of 3-Methyl-2-buten-1-yl Acetate by Treatment of Isoprene With Excess Acetic Acid in the Presence of a Strong Acid Catalyst $K_a>10^2$)

To a solution of 195 mg (1.03 mmoles) of p-toluenesulfonic acid monohydrate in 15 ml of glacial acetic acid was added 1.00 ml (10.0 mmoles) of isoprene. This mixture, while being continuously protected from exposure to atmospheric moisture, was stirred at room temperature for 3 hours. The product was then isolated by dilution of the reaction mixture with 120 ml of 10% (w/v) aqueous sodium chloride and extraction with 50 ml of pentane. After washing the organic layer in successive order with saturated aqueous sodium bicarbonate (1×50 ml) and saturated aqueous sodium chloride (1×50 ml), it was dried over anhydrous magnesium sulfate and filtered. In order to minimize loss of volatile prenyl acetate, the dried organic layer was then concentrated to a volume of 4–5 ml by removal of most of the pentane by fractional distillation at atmospheric pressure. Residual pentane was then removed by evaporation at reduced pressure to yield 218 mg (17% yield if this were solely prenyl acetate) of crude product, shown by proton NMR analysis to be a complex mixture of prenyl acetate (less than one-half of the mixture) and higher molecular-weight by-products. Hence the conversion of isoprene to the desired ester was only 5–10% (at best) using a carboxylic acid in the presence of a strong acid catalyst ($K_a>10^2$). Not only was this process slow (i.e., reaction was incomplete after 3 hours), but it was also inefficient (more isoprene was converted to higher molecular-weight by-products than to the desired prenyl ester). The addition of sodium acetate to improve the efficiency of the process (i.e., by "trapping" the prenyl cation) is not feasible since it would neutralize the strong acid catalyst, thereby preventing any reaction from occurring.

What is claimed:

1. A method of preparing prenyl esters comprising the steps:
   (a) forming a liquid solution containing at least one carboxylic acid of the formula:

RCOOH where R is a substituent selected from the group consisting of H, and $C_1$ haloalkyl through $C_4$ haloalkyl, and the $K_a$ of RCOOH, relative to water, is greater than $10_{-4}$, and wherein no component in said liquid solution has a $K_a$, relative to water, greater than $10^2$;
   (b) slowly adding isoprene to the liquid solution to from a reaction mixture while maintaining said carboxylic in molar excess; and
   (c) isolating prenyl esters from the reaction mixture.

2. The method of claim 1 wherein said liquid solution further contains a base:

$(R'COO)_xM$ wherein R' is H or an organic group, M is a Group I or Group II cation, x is 1 or 2, and R' can be the same or different than R.

3. The method of claim 1 wherein R is dichloromethyl.

4. The method of claim 1 wherein said liquid solution comprises a mixture of carboxylic acids, and one of said acids comprises dichloroacetic acid.

5. The method of claim 2 wherein R' is a substituent selected from the group consisting of H and $C_1$ to $C_4$ haloalkyl.

6. The method of claim 2 further comprising the step:
   maintaining said reaction mixture at a temperature between about 20° C. and 25° C. during said isoprene addition.

7. The method of claim 1, wherein RCOOH comprises formic acid, and said reaction mixture is maintained in a pressure vessel at a temperature of between about 40° C. and 100° C. during said isoprene addition.

8. The method of claim 7 wherein said liquid solution contains a base selected from the group consisting of sodium and potassium salts of a carboxylic acid, or mixtures thereof.

9. The method of claim 2 wherein isoprene is added to the liquid solution in dropwise fashion, over a period of several hours.

10. A method of preparing prenyl alcohol comprising the steps:
    (a) forming a liquid solution comprising dichloroacetic acid and an organic base:

$M(OOCCHCl_2)_x$ wherein M is a Group I or Group II cation and x is 1 or 2;
    (b) slowly adding isoprene to the liquid solution to form a reaction mixture while maintaining dichloroacetic acid in molar excess to produce prenyl dichloroacetate;

(c) partitioning the reaction mixture between water and a non-polar organic solvent whereby prenyl dichloroacetate is in said non-polar solvent; and (d) contacting the partitioned prenyl dichloroacetate with an aqueous solution containing a second base to form prenyl alcohol.

11. The method of claim 10 further including the step: removing the non-polar organic solvent from the prenyl dichloroacetate prior to step (d).

12. The method of claim 10 wherein said second base is selected from the group consisting of sodium hydroxide, potassium hydroxide, sodium carbonate, potassium carbonate, and mixtures thereof.

13. The method of claim 10 further including a step for isolating prenyl alcohol from said aqueous solution comprising:

extracting the aqueous solution with a second organic solvent to form an organic solution containing prenyl alcohol.

14. The method of claim 13 further including a step for recovering liberated dichloroacetic acid from said aqueous solution subsequent to extraction with a second organic solvent comprising:

neutralizing said aqueous solution with an inorganic acid; and extracting the neutralized aqueous solution with a third organic solvent.

15. The method of claim 10 wherein said organic base is sodium dichloroacetate or potassium dichloroacetate.

16. The method of claim 10 wherein said liquid solution contains a second carboxylic acid in addition to dichloroacetic acid.

17. The method of claim 16 wherein the second carboxylic acid is selected from acetic acid and propionic acid.

18. The method of claim 16 wherein the second carboxylic acid comprises a compound of the formula:

RCOOH wherein R is H or an organic group and the $K_a$ of RCOOH, relative to water, is greater than $10^{-4}$.

* * * * *

UNITED STATES PATENT AND TRADEMARK OFFICE
CERTIFICATE OF CORRECTION

PATENT NO. : 5,872,277
DATED : February 16, 1999
INVENTOR(S) : James H. Babler

It is certified that error appears in the above-identified patent and that said Letters Patent is hereby corrected as shown below:

| | |
|---|---|
| Col. 12, line 22 | after "...is greater than", the term "$10_{-4}$" should be, -- $10^{-4}$ --. |
| Col. 12, line 25 | after "...liquid solution to", please delete "from" and insert -- form --. |
| Col. 12, line 26 | after "...maintaining said carboxylic" please insert -- acid --. |

Signed and Sealed this

Sixth Day of July, 1999

Attest:

Q. TODD DICKINSON

*Attesting Officer*　　*Acting Commissioner of Patents and Trademarks*